(12) United States Patent
Uchi et al.

(10) Patent No.: US 7,597,806 B2
(45) Date of Patent: Oct. 6, 2009

(54) BODY FLUID TREATING FILTER DEVICE

(75) Inventors: Yukihiko Uchi, Tokyo (JP); Takeshi Sukegawa, Tokyo (JP)

(73) Assignee: Asahi Kasei Kuraray Medical Co., Ltd., Tokyo (JP)

( * ) Notice: Subject to any disclaimer, the term of this patent is extended or adjusted under 35 U.S.C. 154(b) by 91 days.

(21) Appl. No.: 11/915,045

(22) PCT Filed: May 22, 2006

(86) PCT No.: PCT/JP2006/310168
§ 371 (c)(1),
(2), (4) Date: Jan. 24, 2008

(87) PCT Pub. No.: WO2006/126497
PCT Pub. Date: Nov. 30, 2006

(65) Prior Publication Data
US 2009/0078636 A1    Mar. 26, 2009

(30) Foreign Application Priority Data
May 23, 2005    (JP)    ............................. 2005-149442

(51) Int. Cl.
*B01D 35/30* (2006.01)
*B01D 27/08* (2006.01)
*B01D 29/15* (2006.01)
(52) U.S. Cl. ...................................... 210/232; 210/446
(58) Field of Classification Search ................. 210/232, 210/446
See application file for complete search history.

(56) References Cited

U.S. PATENT DOCUMENTS
4,490,254 A * 12/1984 Gordon et al. ............... 210/247

(Continued)

FOREIGN PATENT DOCUMENTS
JP        62-243561        10/1987

(Continued)

OTHER PUBLICATIONS
English Language Abstract of JP 8-173528.

(Continued)

*Primary Examiner*—Thomas M Lithgow
(74) *Attorney, Agent, or Firm*—Greenblum & Bernstein, P.L.C.

(57) ABSTRACT

A body fluid treating filter device capable of maintaining its treating pressure within a clinically safe pressure range even if body fluid treatment is performed over a long period and having excellent property for recovering a body fluid after the body fluid treatment is completed. A body fluid treating cylindrical filter layer is stored in a cylindrical container having two body fluid flow ports. The cylindrical filter layer is disposed so that the inner space of a container can be divided into two parts by making its both end parts fluid-tight and fixing at least one of these both end parts to the inner wall surface of the container. One of the inner spaces of the container divided by the cylindrical filter layer is allowed to communicate with the first body fluid flow port and the other of the inner spaces of the container divided by the cylindrical filter layer is allowed to communicate with the second body fluid flow port. The body fluid treating cylindrical filter device is characterized in that a bar-like flow passage resistant member extending along the center axis is installed in the hollow part of the cylindrical filter layer, and a spacer layer for flowing the body fluid of 0.7 to 3.5 mm in thickness is formed between the outer peripheral surface of the cylindrical filter layer and the container and between the inner peripheral surface of the cylindrical filter layer and the flow passage resistance member.

4 Claims, 8 Drawing Sheets

U.S. PATENT DOCUMENTS

| | | | |
|---|---|---|---|
| 4,806,135 A * | 2/1989 | Siposs | 96/212 |
| 4,919,802 A * | 4/1990 | Katsura | 422/44 |
| 4,932,987 A * | 6/1990 | Molina | 96/212 |
| 4,964,984 A * | 10/1990 | Reeder et al. | 210/188 |
| 5,632,894 A * | 5/1997 | White et al. | 210/436 |
| 5,651,765 A | 7/1997 | Haworth et al. | |
| 6,176,904 B1 * | 1/2001 | Gupta | 96/209 |
| 2007/0007193 A1 | 1/2007 | Uchi et al. | |

FOREIGN PATENT DOCUMENTS

| | | |
|---|---|---|
| JP | 2-099067 | 4/1990 |
| JP | 8-173528 | 7/1996 |
| JP | 9-201412 | 8/1997 |
| JP | 9-239022 | 9/1997 |
| JP | 9-508564 | 9/1997 |

OTHER PUBLICATIONS

English Language Abstract of JP 2-099067.
English Language Abstract of JP 9-201412.
English Language Abstract of JP 9-239022.

* cited by examiner

Length of the container

BODY FLUID TREATING FILTER DEVICE

TECHNICAL FIELD

The present invention relates to a body fluid-treating filter device packed with a body fluid-treating filter material for effectively removing specific components from a large amount of body fluid such as blood, plasma, and lymph fluid. The present invention further relates to a body fluid-treating filter device packed with a body fluid-treating filter material for changing the functions of components contained in a large amount of body fluid such as blood, plasma, and lymph fluid.

BACKGROUND ART

In recent years, there is an increasing demand for technologies for removing specific proteins, leukocytes, toxins, and the like contained in body fluids of patients to be applied to an extracorporeal circulation blood purification therapy of curing autoimmune diseases, such as systemic lupus erythematosus, chronic or malignant articular rheumatism, multiple sclerosis, chronic ulcerative colitis, and Crohn's disease, as well as other diseases such as sepsis, inflammatory bowel disease, leukemia, and cancer, or for immunity control before an organ transplant operation.

High reliability to safety as a medical device apparatus, not to mention high removing capability of the materials to be removed, is required for a body fluid-treating filter device used in these applications. For example, as a leukocyte-removing filter apparatus well known as an example of the above filter apparatus, a flat-type filter device in which non-woven fabric made from ultra-thin fibers or a filter device equipped with a housing packed with a filter material wound in a cylindrical form (for example, Patent Document 1) are widely used.

A structure of a body fluid-treating filter device will be outlined. FIGS. 6 and 7 show commonly used typical flat-type or cylindrical-type body fluid-treating filter devices. In the figures, a body fluid-treating filter layer 12 formed in the form of a flat plate or a cylinder is housed in a housing 11.

In the cylindrical body fluid-treating filter device of FIG. 7, one end of the filter layer 12 is completely sealed with a dish 16, the other end of the filter layer 12 is liquid-tightly secured to the inside of the lid 18, which has a body fluid flow port 52, and the hollow section 20 of the filter layer 12 communicates to the outside of the device.

If the body fluid to be treated is introduced in this structure from the body fluid flow port 51 (in this case, a body fluid inlet port), the body fluid flows through the filter layer 12 and is sent to the outside from the body fluid flow port 52 (in this case, a body fluid outlet port), while filling the void between the inner wall of the housing 11 and the surface of the filter layer 12. Arrows in the Figures indicate the directions in which the body fluid flows.

In some cases, the device may be operated by causing the body fluid to flow in the directions opposite to the direction of the arrows. In these embodiments, if the body fluid is introduced from the body fluid flow port 52 (in this case, a body fluid inlet port), the body fluid flows through the filter layer 12 and is sent to the outside from the body fluid flow port 51 (in this case, a body fluid outlet port), while filling the void between the inner wall of the housing 11 and the surface of the filter layer 12.

When such a body fluid-treating filter device is actually used, the pressure in the device increases in some cases depending on the state of the blood to be treated, for example, when the amount of a blood anticoagulant added is insufficient or the blood anticoagulant is mixed only insufficiently. In other cases, when a physiological solution is caused to flow in order to recover the blood from the filter device, the physiological solution does not necessarily flow through the entire filter device, resulting in insufficient recovery of the body fluid. In particular, in the flat-type body fluid-treating filter device of FIG. 6, there was a problem of uneven flow of the body fluid introduced from the body fluid flow port 51, since such a body fluid flows through the void between the inner wall of the housing 11 and the surface of the filter layer 12, while spreading two dimensionally.

In addition, a filter device containing a body fluid-treating filter material cylindrically wound around a core pipe having a porous section has been disclosed (Patent Document 2). Although this filter device has an effect of efficiently filling a body fluid-treating filter in a housing, countermeasures against the pressure increase and blood poor recovery were still insufficient since the essential structure remained the same as above.

As mentioned above, commonly used fluid-treating filter devices have problems besides basic performance that should be still improved as a medical apparatus.
[Patent Document 1] JP-A-62-243561
[Patent Document 2] JP-A-9-239022

DISCLOSURE OF THE INVENTION

Problems to be Solved by the Invention

In view of these problems in commonly used technologies, an object of the present invention is to provide a body fluid-treating filter device which can maintain the treating pressure of the filter device in a clinically safe range during operation for a long period of time and can exhibit excellent body fluid recovery performance after completion of a body fluid treatment.

Means for Solving the Problems

As a result of extensive studies with an objective of solving the above problems, the present inventors have found that it is important to appropriately control the flow distribution of a fluid in a body fluid-treating filter device. Specifically, the inventors have found that the flow distribution of a fluid inside the device can be improved by causing the body fluid to be treated to extensively flow from near the end of a plate-like or cylindrical filter having an end surface and disposing a specific spacer layer in several gaps in the body fluid-treating filter device, whereby the problems in generally-used technologies can be totally solved. This finding has led to the completion of the present invention.

Accordingly, the present invention provides:
(1) A cylindrical body fluid-treating filter device comprising a cylindrical housing which has two body fluid flow ports and a body fluid-treating cylindrical filter layer housed in the cylindrical housing, the cylindrical filter layer being disposed so as to divide the inner space of the housing into two hollow sections by liquid-tightly sealing the both ends and securing at least one end thereof to the inner wall of the housing, one of the hollow sections of the housing divided by the cylindrical filter layer communicating with the first body fluid flow port, and the other hollow section in the housing divided by the cylindrical filter layer communicating with the second body fluid flow port, wherein a rod-shaped flow passage resistant member extends through the hollow section along the center axis formed by the cylindrical filter layer, and a spacer layer for allowing a body fluid to flow with a thickness of not less than 0.7 mm, but not more than 3.5 mm, is provided between the outer circumference of the cylindrical filter layer and the housing, and between the inner peripheral surface of the cylindrical filter layer and the flow passage resistant member.

(2) The cylindrical body fluid-treating filter device according to (1) above, wherein the spacer layer for flowing a body fluid with a thickness of not less than 0.7 mm, but not more than 3.5 mm, provided between the inner peripheral surface of the cylindrical filter layer and the flow passage resistant member extends ¼ to ¹⁵⁄₁₆ of the length of the hollow section from one end of the cylindrical filter layer.

(3) The cylindrical body fluid-treating filter device according to (1) or (2) above, wherein the flow passage resistant member has a shape of which the cross-sectional area is fixed on the side near the end of the cylindrical filter layer, but continuously or intermittently decreases toward the other end.

Effect of the Invention

The body fluid-treating filter device of the present invention can maintain the treating pressure of the filter device in a clinically safe range during operation for a long period of time and can exhibit excellent body fluid recovery performance, leaving only a small amount of reside in the device after completion of a body fluid treatment.

EXPLANATION OF SYMBOLS

Figure 1:
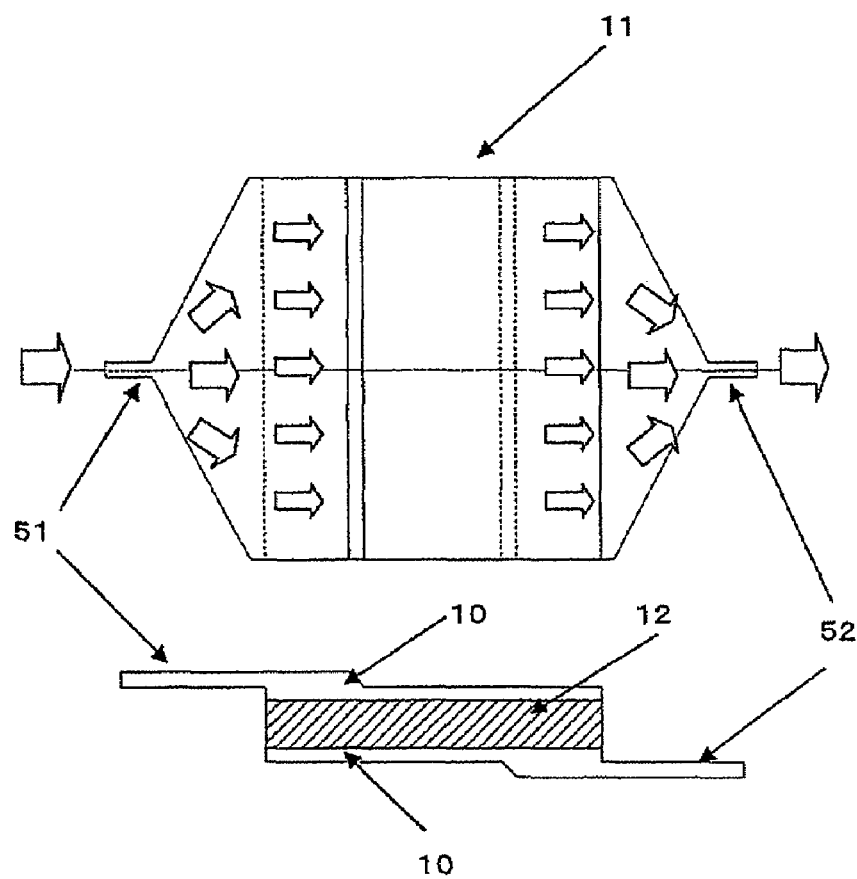
FIG. 1 is a schematic front cross-sectional view of one example of a plate-like body fluid-treating filter device according to the present invention.

10: Spacer layer
11: Housing of a filter layer
12: Body fluid-treating filter layer
13: Outer spacer layer
14: Inner spacer layer
15: Flow passage resistant member
16: Dish (one end)
17: Lid having body fluid flow port
18: Lid having body fluid flow port
19: Sealing cap
20: Hollow section
51: Body fluid flow port (inlet port)
52: Body fluid flow port (outlet port)

BEST MODE FOR CARRYING OUT THE INVENTION

The body fluid-treating filter device of the present invention is a device having a body fluid-treating filter material which is liquid-tightly housed in a housing equipped with body fluid flow ports used as an inlet port and an outlet port of a body fluid. It is used as a filter or an adsorber of a body fluid such as blood, plasma, and lymph fluid. There is a body fluid-treating filter device for returning body fluid components which have deteriorated due to various diseases into a normal state, a body fluid-treating filter device for changing the immunity capability of a biological entity, and the like.

For example, a blood cell/plasma separator for filtering plasma containing malignant substances such as self-antibodies and immune complex, which is used for a collagen disease, an autoimmune disease, and the like, a filter for selectively removing high molecular weight material which contain malignant substances from plasma, an adsorber for selectively adsorbing malignant substances from plasma, an adsorber for adsorbing poisonous substances from the blood of a drug-poisoned patient, an adsorber for adsorbing bilirubin from the blood of a liver disease patient, an adsorber for adsorbing a blood-type substance from blood of a blood-type incompatibility pregnancy patient, a blood separation filter for removing leukocytes and lymphocytes from the blood of an autoimmune disease patient, a blood cell separation filter for removing leukemia cells from the blood of a leukemia patient, a cell-stimulating device for stimulating immunocompetent cells in blood to induce a specific function, and the like can be given as examples of the body fluid-treating filter device.

FIG. 1 is a cross-sectional view showing a typical structure. As previously described referring to FIG. 6 in the chapter of the Background Art, a body fluid-treating filter layer 12 formed in the shape of a plate is housed in a housing 11, and a spacer layer 10 with a gap of 0.7 to 3.5 mm from the internal circumference of the housing is provided on both sides of the body fluid-treating filter layer 12. The body fluid to be treated is introduced from a body fluid flow port 51 into the spacer layer through the entire end face of the body fluid-treating filter layer. The body fluid passing through the body fluid-treating filter layer flows to a spacer layer on the opposite side, and is discharged out of the housing from a body fluid flow port through the other entire end face of a body fluid-treating filter layer.

Figure 6:
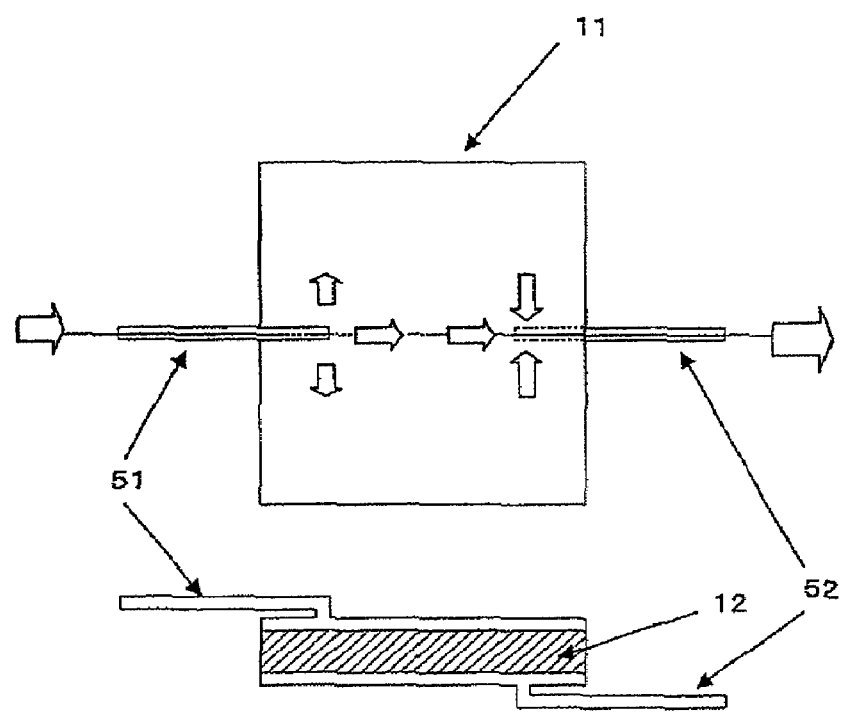
FIG. 6 is a schematic diagram showing a front cross-sectional view of a commonly-used plate-like body fluid-treating unit.

According to the present invention, a body fluid flows in from the entire end face of the filter layer and passes through the above-mentioned specific spacer layer, whereby, differing from the commonly-used technique shown in FIG. 6, the body fluid flows almost uniformly at a certain flow rate on the surface of the filter layer in one direction. In this manner, an uneven flow in the filter layer can be prevented. Moreover, since it is possible to cause a body fluid to flow to the end of the filter by appropriately selecting the thickness of the filter layer, a short pass of the filter layer can be prevented and, consequently, the pressure loss of the device can be reduced. This ensures a long life of the device and reduces the amount of residual blood during a washing operation.

If the thickness of the spacer layer is less than 0.7 mm, the pressure loss of the body fluid flowing through the spacer layer increases. Not only it is difficult to maintain a uniform flow through the filter layer, but also a rapid increase in the pressure rise in the entire device occurs. On the other hand, if the thickness is more than 3.5 mm, although a uniform flow of a body fluid through the entire filter layer can be ensured and the pressure loss in the entire device can be reduced, the body fluid cannot flow smoothly in some parts of the device due to an increase in the volume of the spacer layer. In addition, the amount of residual blood during washing increases.

It is possible to intentionally reduce the amount of a body fluid filtered near the end of the filter by increasing the thickness of the spacer layer near the end as shown in FIG. 1, whereby the amount of residual blood during washing can be decreased.

The area with an increased thickness is preferably about 1/16 to 3/4 of the length of the filter layer in the direction of the body fluid.

Figure 2:
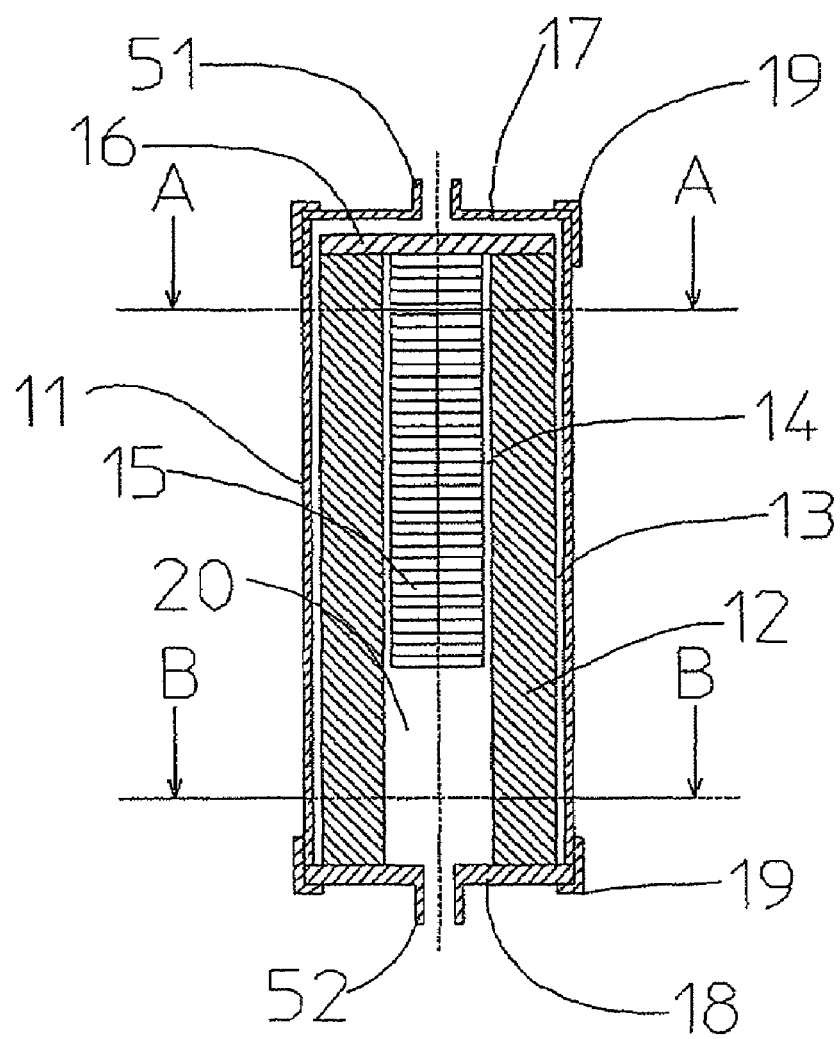
FIG. 2 is a schematic front cross-sectional view of one example of a cylindrical body fluid-treating filter device according to the present invention.
Figure 3:
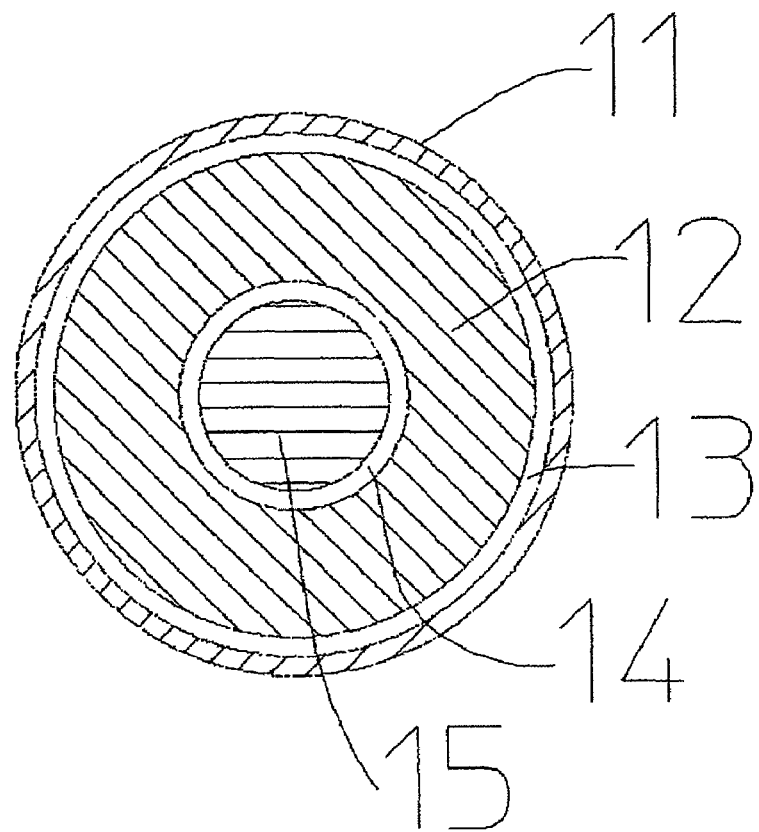
FIG. 3 is a cross-sectional view along the A-A line of one example of a cylindrical body fluid-treating filter device according to the present invention.
Figure 4:
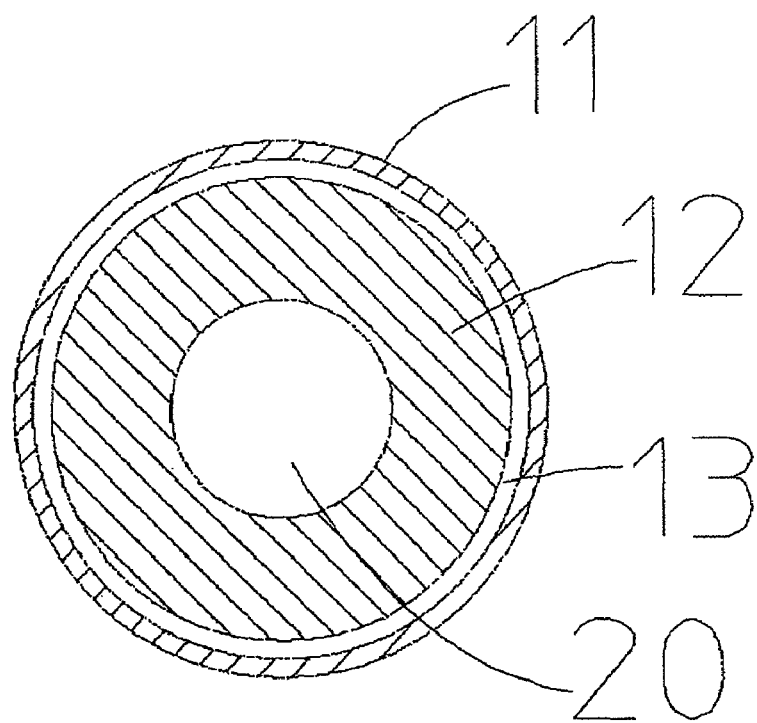
FIG. 4 is a cross-sectional view along the B-B line of one example of a cylindrical body fluid-treating filter device according to the present invention.
Figure 7:
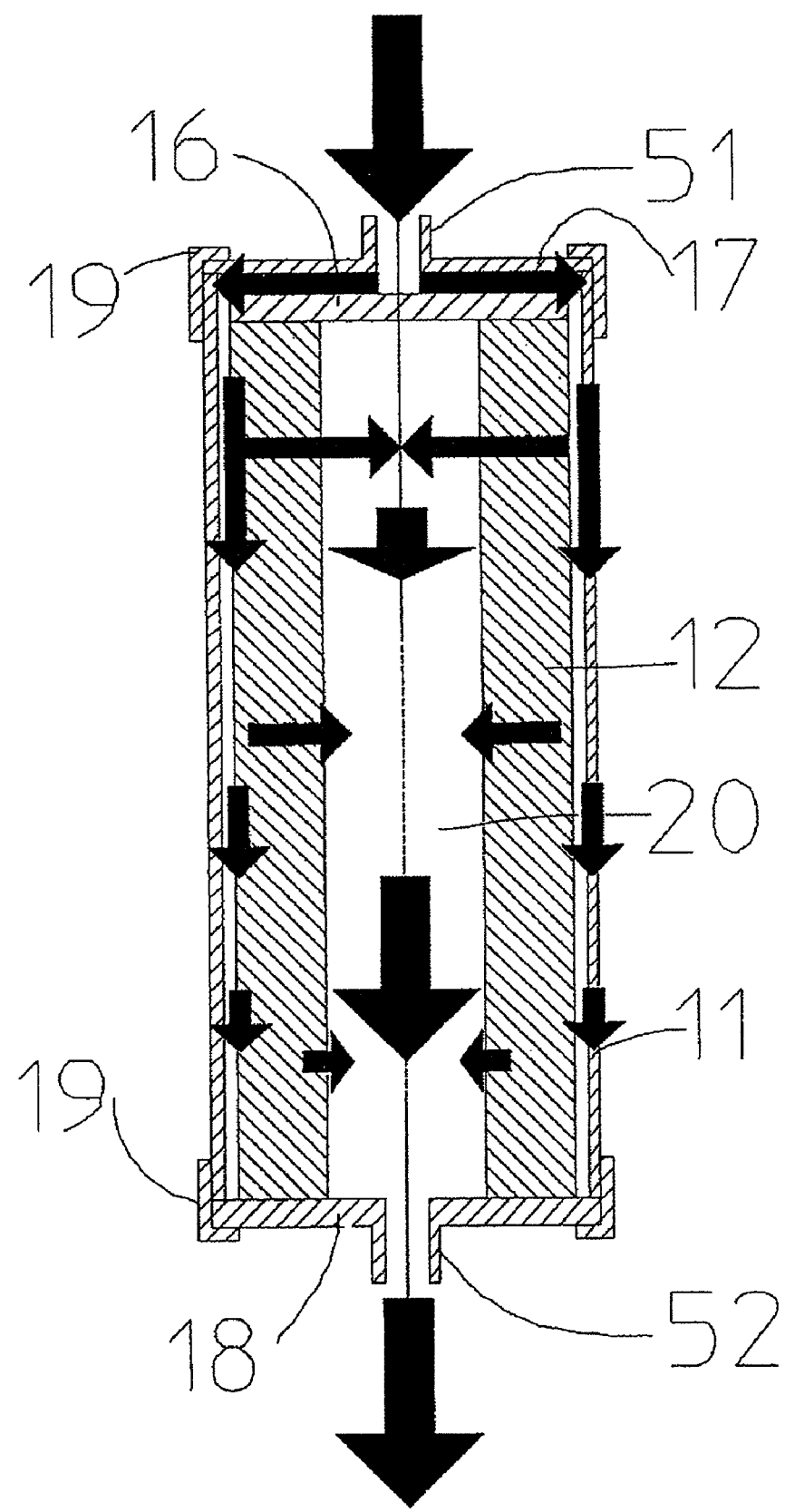
FIG. 7 is a schematic diagram showing a flow of a body fluid when a flow passage resistant member is not provided in a commonly-used cylindrical body fluid-treating unit.

FIG. 2 is a cross-sectional diagram showing a typical structure of a cylindrical body fluid-treating filter device. In FIG. 2, a body fluid-treating filter layer formed in a cylindrical shape is installed inside a cylindrical housing 11, and one end of the filter layer 12 is completely sealed with a dish 16. The other end of the filter layer 12 liquid-tightly secured to the inside of a lid 18 which has a body fluid flow port 52, and a hollow section 20 of the filter layer 12 communicates to the outside of the device. In the same manner as in the device shown in FIG. 7, the body fluid to be treated flows either in the direction from the body fluid flow port 51 (the body fluid inlet port) to the body fluid flow port 52 (the body fluid outlet port) or in the opposite direction.

The body fluid-treating filter layer used in the present invention is formed from a filter material which can remove specific blood cells, proteins, toxins, and the like from a body fluid such as blood. Such a filter material is preferably a material which can selectively entrap the blood cells, proteins, toxins, and the like to be removed.

The filter layer may be made from a material which can entrap or adsorb the object to be removed by utilizing the physical and chemical properties of the material itself, or a material containing a ligand having selective affinity with the object to be removed immobilized thereon. Of course, a filter layer material having these properties in combination can be used. A specific filter layer material can be appropriately selected according to the object to be removed. In order to improve selectivity of the object to be removed, a material whereof the surface has been modified by polymer coating, grafting, or immobilization of a ligand as disclosed in JP-B-6-51060 is preferably used.

As a form of the filter layer, a plate-like or a hollow cylindrical formed material made from a sheet-like bag packed with particles or sheets of nonwoven fabric, woven fabric, or a porous material can be given. When leukocytes are removed, the use of nonwoven fabric, woven fabric, or a porous material as a filter material is preferable from the viewpoint of removal efficiency. As the fiber material used for the nonwoven fabric or woven fabric, synthetic fiber, inorganic fiber, and the like can be used. Among these, polyesters such as polyethylene terephthalate and polybutylene terephthalate, nylon, polyolefins such as polypropylene and polyethylene, a polystyrene resin, and synthetic fiber such as polyacrylonitrile are preferably used.

The filter layer may be a plate-like or hollow cylindrically-formed article made from either a single filter material or a combination of two or more filter materials. When a combination of two or more types of nonwoven or woven fabric is used, use of filter materials with different average fiber diameters or different filling densities is effective in order to increase the removal performance and removal speed. Also, in the case of a sheet of a porous material, it is preferable to combine sheets with different average pore sizes. In addition, a nonwoven fabric, a porous material sheet, particles formed into a sheet, and the like may be combined.

The housing 11 of the present invention consists of two or more parts to house the filter layer therein. In the plate-like body fluid-treating filter device shown in FIG. 1, the housing 11 is a casing dividable into two or more parts, each having a body fluid flow pipe. In the cylindrical body fluid-treating filter device shown in FIG. 2, the housing 11 has a cylinder for housing the filter layer 12, a lid 17 having a body fluid flow port 51 and a lid 18 having a body fluid flow port 52, each covering the ends of the cylinder, and a pair of sealing caps 19 which liquid-tightly secures the lid 17 and lid 18 to the cylinder. It should be understood that these are typical structures and that the housing structure is not limited to these insofar as the same flow of the body fluid as in the body fluid-treating filter device of the present invention can be ensured. There are no particular limitations to the material used for the housing of the present invention. General purpose resins such as polycarbonate, polysulfone, polypropylene, nylon 6, nylon 12, polyethylene terephthalate, polyethylene, and Teflon(trade mark) can be suitably used.

The body fluid-treating device of the present invention is characterized by being provided with spacer layers 10, 13, and 14 having a thickness of 0.7 to 3.5 mm, on both filtration surfaces of the body fluid filter layer 12. The spacer layer as used in the present invention refers to a space between the housing wall and the outer surface of the body fluid-treating filter layer, and a layer which controls the flow of a treated fluid in the space formed by the body fluid-treating filter layer. In the case of a cylindrical filter, the spacer layer refers to the space formed by the innermost cylindrical filter layer or the space between the innermost cylindrical filter layer and the flow passage resistant member.

Figure 5:
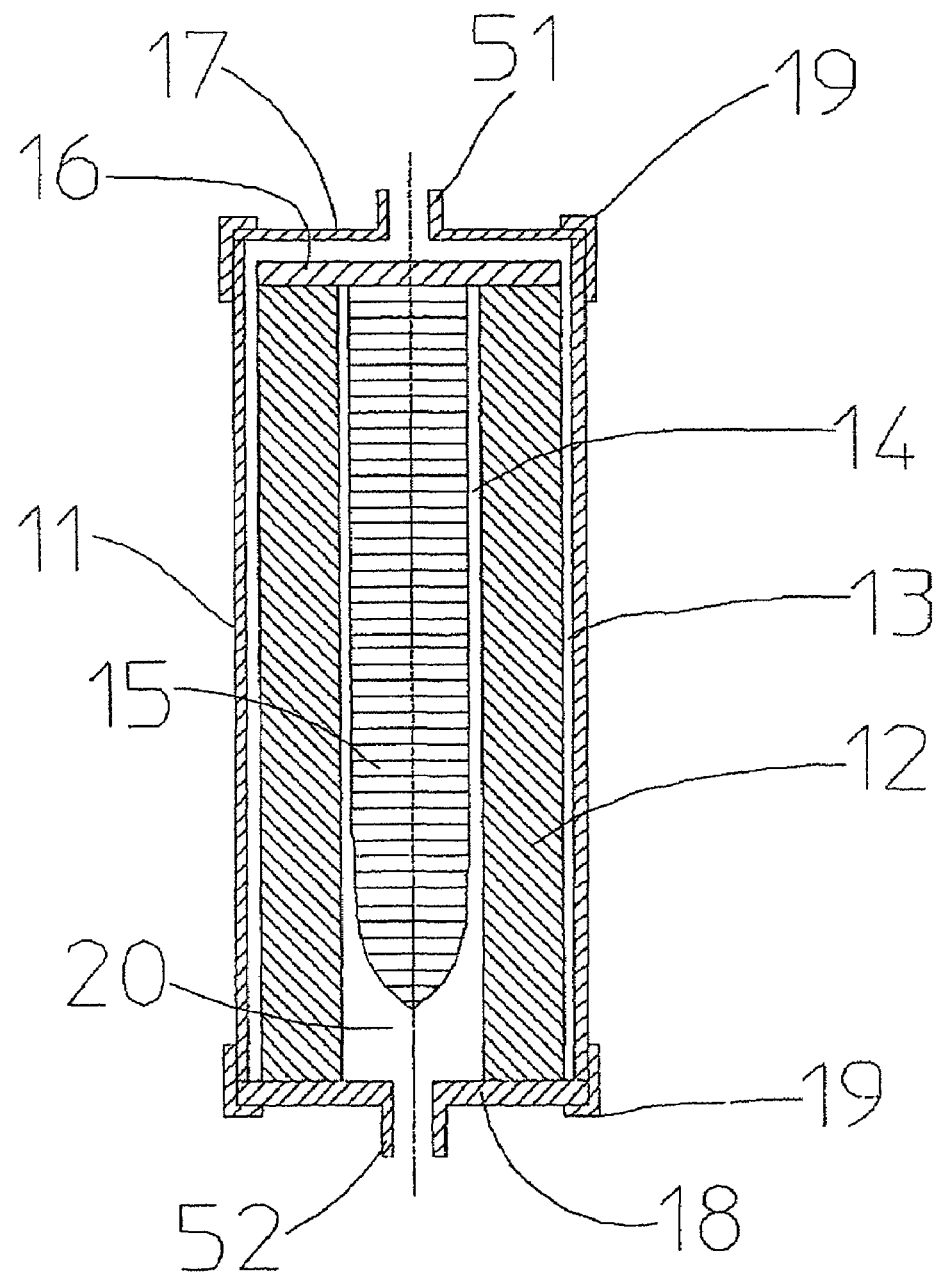
FIG. 5 is a schematic front cross-sectional view of one example of a body fluid-treating filter device according to the present invention, in which the cross-sectional area of a flow passage resistant member changes.
Figure 8:
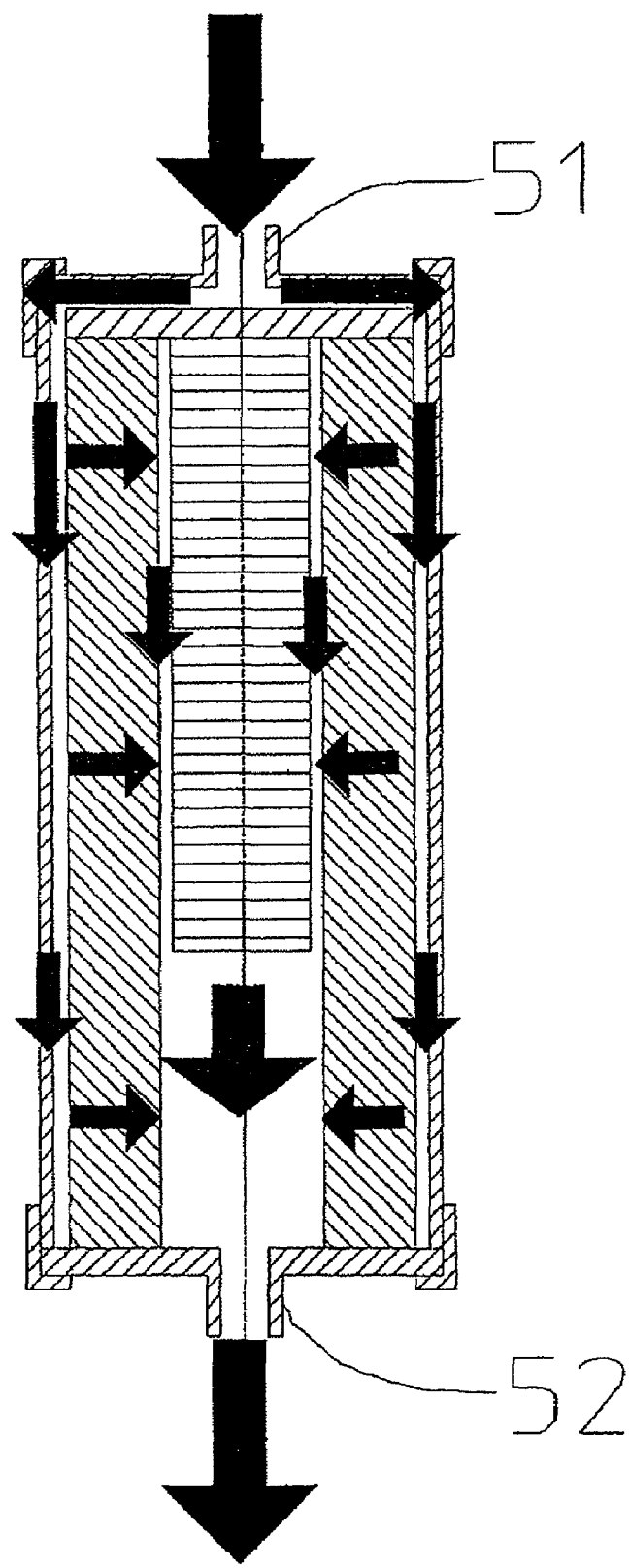
FIG. 8 is a schematic diagram showing a flow of a body fluid when a flow passage resistant member is provided in the cylindrical body fluid-treating device of the present invention.

In the case of a cylinder-type body fluid-treating device, the hollow section of a cylindrical filter layer can be the spacer layer 14 of the present invention, if the diameter is more than twice the thickness of the usual spacer layer, that is, if the diameter is between 1.4 mm and 7.0 mm. When the diameter of the hollow section is more than 7.0 mm, a spacer layer with a thickness 0.7 to 3.5 mm, as a gap between the outer surface of the flow passage resistant member and the inner surface of the filter layer, can be formed by providing a flow passage resistant member 15 in the hollow section 20 of filter layer 12, as shown in FIG. 2, FIG. 5, and FIG. 8.

The flow passage resistant member 15 in the present invention refers to a component provided in the hollow section 20 on the inner peripheral surface of the body fluid-treating filter layer 12, extending from one end 16 of the filter layer 12 on the side of the body fluid flow port 51 in the direction of the body fluid flow port 52 communicating with the hollow section 20. The flow passage resistant member 15 creates a pressure loss in the flow passage by narrowing the cross-sectional area of the hollow section.

Any material such as a rod-shaped article that can resist flow of a fluid in the hollow section can be used as the flow passage resistant member 15. A solid rod, a hollow rod, a porous body, and the like can be given as specific examples. A solid rod or a hollow rod is preferable from the viewpoint of ease of handling. Any material that can be suitably used as a medical application component can be used for the flow passage resistant member. The same material as that of the housing may be used.

The flow passage resistant member may have a shape with a fixed cross-section lengthwise or a shape tapering, partly or through the entire length, toward the body fluid flow port 52 communicating with the hollow section. A shape of which the cross-section conically tapers toward the body fluid flow port 52 leading to the hollow section, in particular, a shape of which the cross-section does not change or changes only slightly in the area near the body fluid flow port 51 communicating with the outer surface of the filter material, is preferably used. One example of such a shape is shown in FIG. 5.

The length of the flow passage resistant member is preferably such that the length of the part in which the gap between the flow passage resistant member and the filter layer inner surface is 0.7 to 3.5 mm toward the body fluid flow port 52 communicating with the hollow section, fluid-treating filter layer is from $1/4$ to $15/16$, and particularly $3/4$, of the length of the hollow section. If the length is less than $1/4$, it is difficult to obtain a uniform flow of a body fluid and the amount of residual body fluid left in the device in the recovery operation using a physiological solution tends to increase. If it is more than $15/16$, the fluid passage resistance increases and the body fluid-treating filter device tends to become easily clogged. A more preferable range is $1/4$ to $3/4$, and it is still more preferably $3/10$ to $13/20$, and particularly preferably $7/20$ to $11/20$.

The spacer layer may be any layer which can form and maintain a certain gap in the above-mentioned space, specifically, a space in the shape of a layer formed by a spacer material such as a mesh sheet or a porous sheet. On the other hand, a spacer material may be provided by producing irregularities on the wall of a cylindrical housing or on the outer surface of the flow passage resistant member, or by disposing a material equivalent to the irregularities. A mesh sheet is preferable from the viewpoint of ease of handling and protecting the outer surface of the body fluid-treating filter material.

To ensure easy flow in the spacer layer, the product of the air permeability and the thickness of the spacer material is preferably 50 times or more, and more preferably 100 times or more the product of the air permeability and the thickness of the filter material in the case of a sheet-like spacer material. If the product of the air permeability and the thickness of the spacer material satisfies this condition, the spacer material may be the same material as the body fluid-treating filter material (for example, nonwoven fabrics with a different specification). A product produced by stacking these materials is preferable for ensuring a uniform flow of a body fluid.

When the body fluid-treating filter material is formed from two or more filter layers with different specifications and the outermost circumference of the filter material is directly in contact with the inner surface of the housing, the outermost layer is regarded as a spacer layer to the extent that the product of the air permeability and the thickness of the outermost filter layer is 50 times or more the product of the air permeability and the thickness of the inner filter layer. On the other hand, when the innermost circumference is directly in contact with the surface of the flow passage resistant member, the innermost layer is regarded as the spacer layer to the extent that the product of the air permeability and the thickness of the innermost filter layer is 50 times or more the product of the air permeability and the thickness of the outer filter layer. The air permeability is measured according to JIS L1096-A.

The thickness of the spacer layer must be between 0.7 mm and 3.5 mm. If the thickness of the spacer layer is less than 0.7 mm, the flow of a body fluid become extremely poor and the body fluid-treating filter device may become clogged. If the thickness is more than 3.5 mm, on the other hand, flow of a body fluid becomes uneven even if a flow passage resistant member is provided, increasing the amount of a body fluid remaining in the body fluid-treating filter device when the body fluid is recovered using a physiological solution. A more preferable range of the spacer thickness is from 0.9 mm to 2.5 mm, with a particularly preferable range being 1 mm to 2 mm.

In the case of a cylindrical body fluid-treating unit, the spacer layer is circular and the thickness is $1/2$ of the difference of the inner diameter and the outer diameter of the ring. Specifically, the thickness of the outer spacer layer of the body fluid-treating filter layer is $1/2$ of the difference of the average outer diameter of the filter layer and the average inner diameter of the cylindrical housing, and the thickness of the inner spacer layer of the body fluid-treating filter layer is $1/2$ of the difference of the average outer diameter of the flow passage resistant member and the average inner diameter of the body fluid-treating filter layer. When the filter layer is wound around the outside of the spacer layer of a mesh material as described later in Examples, the thickness of the inner spacer layer was determined from the difference of the average outer diameter of the flow passage resistant member and the average inner diameter of the mesh layer. Note that the thickness of the inner spacer layer is 0 mm when a spacer material is not used, since the filter layer comes in contact with the outer surface of the flow passage resistant member.

As mentioned above, if the thickness of the outer spacer layer is suitably maintained and the pressure loss in the area near the body fluid flow port 51 (in this case, a body fluid inlet port) of the body fluid-treating filter layer is increased by providing a flow passage resistant member in the hollow section of the body fluid-treating filter layer, as shown in FIG. 8, for example, it is possible to control the flow of a physiological saline solution in the area near the body fluid flow port 51 (inlet port) of the inner spacer. As a result, the physiological saline solution sufficiently flows to the area near the body fluid flow port 52 (in this case, a body fluid outlet port) of the body fluid-treating filter layer, whereby sufficient blood recovery can be ensured. The thickness of the arrows in FIG. 8 qualitatively shows flowability of a body fluid, that is, the flow rate magnitude.

The above structure not only reduces fluctuation of the blood flow in the body fluid-treating filter layer during a blood treatment, but also prevents clogging and suppresses a pressure loss due to an increased load at particular locations.

Seemingly, the structure of the device according to the present invention appears to increase the pressure loss by providing a spacer layer. However, since the spacer layer can offset a pressure increase due to an uneven flow, the overall pressure loss of the device does not necessarily increase. In addition, the structure has an unexpected advantage of preventing a rapid pressure increase.

Hereinafter, the present invention will be described in more detail by referring to the examples. However, the present invention is not limited to them.

EXAMPLE 1

(Preparation of Cylindrical Filter Material)

The cylindrical filter layer used in Examples and Comparative Examples was prepared by winding a spacer material used as an inner side spacer layer around a rod-shaped member for assembly to be used as a core in the shape of a roll of cloth, winding a spacer material to be used as an outer side spacer layer while controlling torque to make the external diameter of the outer side spacer 38 mm, and extracting the rod-shaped member.

First, polyethylene mesh (mesh size: 8, thickness: 0.75 mm, width: the same as the housing length), which is the spacer material to be used as the inner side spacer layer, was wound two rounds around the rod-shaped member to make the inner diameter 15 mm or more and the outer diameter 18 mm. Next, as a filter layer, the filter material was directly wound around the rod-shaped member for assembly use (the inner side spacer layer was not provided in Comparative Example 4). After that, the same assembly procedure as above was followed.

From the inner side, 760 mm of nonwoven fabric (density: 98 g/m², thickness: 0.50 mm) made of polyester (PET, density: 1.38 g/cm³) fiber with an average diameter of 2.7 micrometers was wound eleven rounds, 530 mm of nonwoven fabric (density: 102 g/m², thickness: 0.46 mm) made of polyester (PET, density: 1.38 g/cm³) fiber with an average diameter of 12 micrometers was wound five rounds, 800 mm of nonwoven fabric (density: 31 g/m², thickness: 0.19 mm) made of polyester (PET, density: 1.38 g/cm³) fiber with an average diameter of 12 micrometers was wound seven rounds, and 530 mm of nonwoven fabric (density: 50 g/m², thickness: 0.26 mm) made of polyester (PET, density: 1.38 g/cm³) fiber with an average diameter of 33 micrometers was wound 5 rounds. The width of each filter layer was the same as the length of the housing which is described later. Lastly, polyethylene mesh (mesh size: 8, thickness: 0.75 mm, width: the same as the housing length) was wound one round as the outermost spacer material.

(Assembly of Filter Device)

Figure 9:
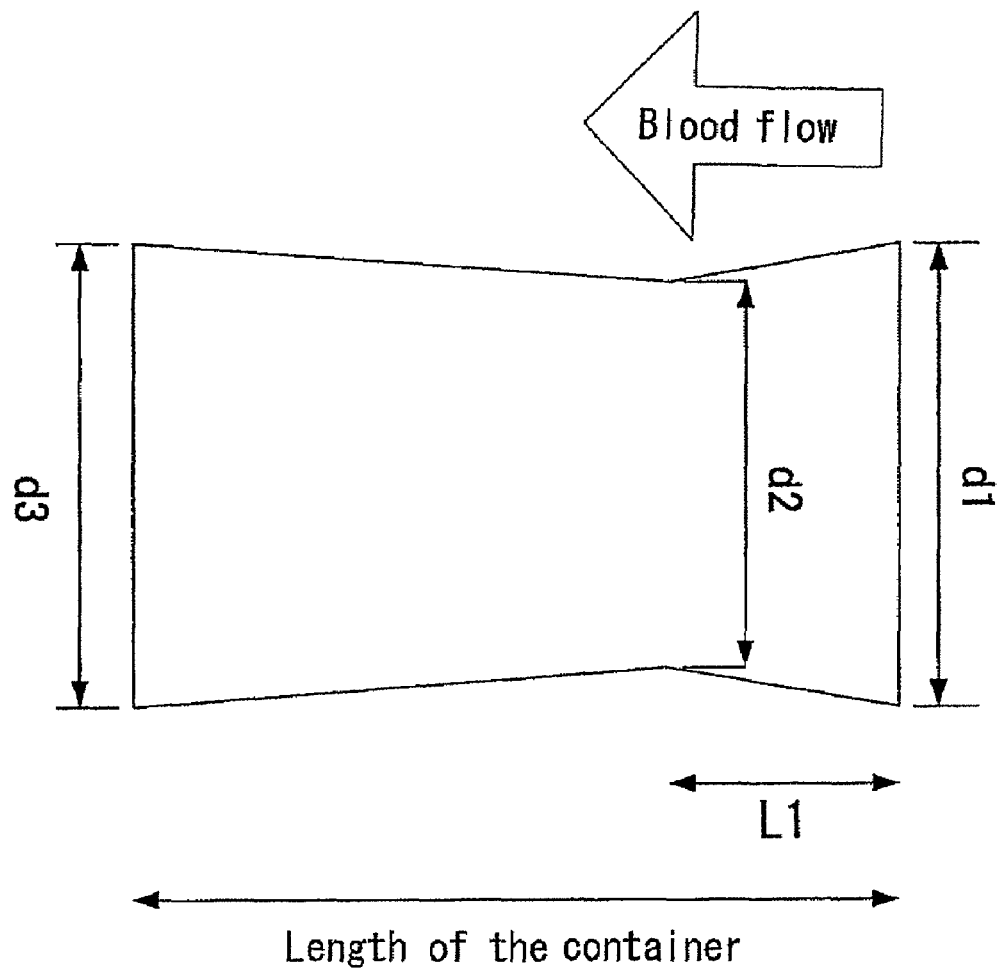
FIG. 9 is a schematic diagram showing a cylinder (a cylindrical housing).

As a flow passage resistant member, a solid stick made of polycarbonate (diameter; 15 mm, total length: 112.5 mm) was prepared. One end of the flow passage resistant member was adhered with polyurethane to the center of a disk-like pan with an inner diameter of 38 mm. The other end was inserted into a hollow section of the body fluid-treating filter material, of which the end was liquid-tightly adhered with polyurethane to the disk-like pan. On the other hand, the other end of the body fluid-treating filter layer was liquid-tightly attached with polyurethane to a lid equipped with a body fluid flow port, thereby connecting the hollow section of the filter layer with the body fluid flow port. The resulting article was inserted in a cylinder (slightly tapered, having dimensions of inner diameter (d1): 42 mm, inner diameter (d2): 41 mm, inner diameter (d3): 42 mm, housing length: 150 mm, L1: 75 mm, average inner diameter: 41.5 mm) made of polycarbonate, shown in FIG. 9, and a lid equipped with a body fluid flow port was liquid-tightly secured to the end of the housing a sealing cap. The other end of the cylinder was covered with a lid equipped with a body fluid flow port and liquid-tightly secured to the end of the housing a sealing cap, thereby obtaining a body fluid-treating filter device shown in FIG. 2.

EXAMPLE 2

A body fluid-treating filter device according to the specification of Example 1 was obtained in the same manner as in Example 1, except that a flow passage resistant member with a diameter of 11 mm was used and polyethylene mesh, which is the spacer material to be used as the inner side spacer layer, was wound four rounds to make the inner diameter 11 mm or more and the outer diameter 18 mm.

EXAMPLE 3

A body fluid-treating filter device according to the specification of Example 1 was obtained in the same manner as in Example 1, except that a flow passage resistant member with a diameter of 18 mm was used and polyethylene mesh (mesh size: 9, thickness: 0.525 mm), which is the spacer material to be used as the inner side spacer layer, was wound one round to make the inner diameter 18 mm or more and the outer diameter 19.4 mm. In this example, in order to make the outer diameter of the outer side spacer layer 38 mm, torque was more tightly controlled than in the filter layer and the outer side spacer layer of the other examples and comparative examples.

EXAMPLE 4

A body fluid-treating filter device according to the specification of Example 1 was obtained in the same manner as in Example 1, except for using a flow passage resistant member with a diameter of 15 mm and a total length of 18.75 mm and a polycarbonate cylinder having dimensions of an inner diameter (d1): 41.2 mm, inner diameter (d2): 39.9 mm, inner diameter (d3): 39.4 mm, housing length: 75 mm, L1: 37.5 mm, and average inner diameter: 40.1 mm.

EXAMPLE 5

A body fluid-treating filter device according to the specification of Example 1 was obtained in the same manner as in Example 1, except for using a flow passage resistant member with a diameter of 15 mm and a total length of 37.5 mm and a polycarbonate cylinder having dimensions of an inner diameter (d1): 41.2 mm, inner diameter (d2): 39.9 mm, inner diameter (d3): 39.4 mm, housing length: 75 mm, L1: 37.5 mm, and average inner diameter: 40.1 mm.

EXAMPLE 6

A body fluid-treating filter device according to the specification of Example 1 was obtained in the same manner as in Example 1, except for using a flow passage resistant member with a diameter of 15 mm and a total length of 56.25 mm and a polycarbonate cylinder having dimensions of an inner diameter (d1): 41.2 mm, inner diameter (d2): 39.9 mm, inner diameter (d3): 39.4 mm, housing length: 75 mm, L1: 37.5 mm, and average inner diameter: 40.1 mm.

EXAMPLE 7

A body fluid-treating filter device according to the specification of Example 1 was obtained in the same manner as in Example 1, except for using a flow passage resistant member with a diameter of 15 mm and a total length of 70.31 mm and a polycarbonate cylinder having dimensions of an inner diameter (d1): 41.2 mm, inner diameter (d2): 39.9 mm, inner diameter (d3): 39.4 mm, housing length: 75 mm, L1: 37.5 mm, and average inner diameter: 40.1 mm.

COMPARATIVE EXAMPLE 1

A body fluid-treating filter device according to the specification of Example 1 was obtained in the same manner as in Example 1, except that a flow passage resistant member was not used and polyethylene mesh, which is the spacer material to be used as the inner side spacer layer, was wound two rounds to make the outer diameter 18 mm.

COMPARATIVE EXAMPLE 2

A body fluid-treating filter device according to the specification of Example 1 was obtained in the same manner as in Example 1, except that a flow passage resistant member was not used, polyethylene mesh, which is the spacer material to be used as the inner side spacer layer, was wound two rounds to make the outer diameter 18 mm, and a polycarbonate cylinder having dimensions of an inner diameter (d1): 42 mm, inner diameter (d2): 41 mm, inner diameter (d3): 42 mm, housing length: 75 mm, L1: 17 mm, and average inner diameter: 41.5 mm was used.

COMPARATIVE EXAMPLE 3

A body fluid-treating filter device according to the specification of Example 1 was obtained in the same manner as in Example 1, except that a flow passage resistant member with a diameter of 10 mm was used and polyethylene mesh, which is the spacer material to be used as the inner side spacer layer, was wound two rounds to make the inner diameter 10 mm or more and the outer diameter 18 mm.

COMPARATIVE EXAMPLE 4

A body fluid-treating filter device according to the specification of Example 1 was obtained in the same manner as in Example 1, except that a flow passage resistant member with a diameter of 18 mm was used and the filter material was wound around the rod-shaped member without using a spacer material which functions as an inner side spacer layer.

The specifications of the body fluid-treating filter devices used for the above Examples and Comparative Examples are shown in Tables 1 to 3. That is, various types of cylinders (cylindrical housings) are shown in Table 1, various types of flow passage resistant members are shown in Table 2, and types of housings, types of the flow passage resistant member, spacer layer thickness, and the ratio of the length of the flow passage resistant member to the length of the housing are shown in Table 3. The flow passage resistant members shown in Table 2 are cylinders with a fixed cross-sectional area in the length direction. A slash in Table 3 indicates that no flow passage resistant member was used.

Since fibers having a circular cross-section are stacked up in the polyethylene mesh material, the maximum thickness is equivalent to twice the fiber diameter and the minimum thickness is equivalent to the fiber diameter. Accordingly, the average value was regarded as the thickness. Specifically, the fiber diameter was 0.5 mm for a mesh size 8 and 0.35 mm for a mesh size 9, and the thickness of the mesh was respectively 0.75 mm and 0.525 mm.

TABLE 1

| | Housing type | | |
|---|---|---|---|
| | A | B | C |
| Inner diameter d1 (mm) | 42 | 42 | 41.2 |
| Inner diameter d2 (mm) | 41 | 41 | 39.9 |
| Inner diameter d3 (mm) | 42 | 42 | 39.4 |
| Housing length (mm) | 150 | 75 | 75 |
| L1 (mm) | 75 | 17 | 37.5 |
| Average inner diameter (mm) | 41.5 | 41.5 | 40.1 |

TABLE 2

| | Flow passage reistant member | | | | | | | |
|---|---|---|---|---|---|---|---|---|
| | 1-1 | 1-2 | 1-3 | 1-4 | 2-1 | 2-2 | 2-3 | 2-4 |
| Diameter (mm) | 15 | 11 | 18 | 10 | 15 | 15 | 15 | 15 |
| Total length (mm) | 112.5 | 112.5 | 112.5 | 112.5 | 18.75 | 37.5 | 56.25 | 70.31 |

TABLE 3

| | Example | | | | | | | Comparative Example | | | |
|---|---|---|---|---|---|---|---|---|---|---|---|
| | 1 | 2 | 3 | 4 | 5 | 6 | 7 | 1 | 2 | 3 | 4 |
| Type of housing | A | A | A | C | C | C | C | A | B | A | A |
| Type of flow passage resistant member | 1-1 | 1-2 | 1-3 | 2-1 | 2-2 | 2-3 | 2-4 | | | 1-4 | 1-3 |
| Outer side spacer layer thickness (mm) | 2.25 | 2.25 | 2.25 | 1.55 | 1.55 | 1.55 | 1.55 | 2.25 | 2.25 | 2.25 | 2.25 |
| Inner side spacer layer thickness (mm) | 1.5 | 3.5 | 0.7 | 1.5 | 1.5 | 1.5 | 1.5 | | | 4 | 0 |
| Length of body fluid-treating filter (mm) | 150 | 150 | 150 | 75 | 75 | 75 | 75 | 150 | 75 | 150 | 150 |
| Length of flow passage resistant member/length of body fluid-treating filter | 0.75 | 0.75 | 0.75 | 0.25 | 0.5 | 0.75 | 0.94 | | | 0.75 | 0.75 |

Next, the pressure increase and body fluid recovery performance of these body fluid-treating filter devices were evaluated. Details of the evaluation method are described below.

<Evaluation of Pressure Increase>

A blood circulation circuit was prepared by connecting a blood circuit equipped with a pressure measurement line and a blood pump to body fluid flow ports (two points of an inlet port side and an outlet port side) of a body fluid-treating filter device and installing a one-day preservation whole blood pool of a cow (erythrocyte concentration: 63,600 to 81,000 cells/µl), to which an anticoagulant was added. The blood was circulated through the circuit at a prescribed flow rate, while monitoring the pressure difference of the internal pressure of the circuit at the inlet port side and the outlet port side of the body fluid-treating filter device. The pressure difference at the time of reaching a predetermined blood throughput was regarded as the treating pressure increase value.

Taking the difference in the volume of the body fluid-treating filter devices into consideration, 2,000 ml of blood was treated at a flow rate of 50 ml/min in the group with a large capacity (Examples 1 to 3 and Comparative Examples 1, 3, and 4) and 1,000 ml of blood was treated at a flow rate of 25 ml/min in the group with a smaller capacity (Examples 4 to 7 and Comparative Example 2).

In this evaluation, the pressure increase was judged by whether or not the treating pressure increase value reaches 100 mmHg or not under the above-mentioned conditions. This is because hemolysis does not occur easily during extracorporeal circulation or the like if the treating pressure is not more than 100 mmHg.

(Measurement of Amount of Recovered Body Fluid)

The same blood circulation circuit as used in the evaluation of the treating pressure increase was prepared. Using this blood circulation circuit, (1) a prescribed amount of a one-day preservation whole blood pool of a cow (erythrocyte concentration: 63,600 to 81,000 cells/μl), to which an anticoagulant was added, was circulated through a body fluid-treating filter device. Next, using this circuit as a one-through circuit, (2) blood in the device and the circuit was collected using a prescribed amount of a physiological saline solution, (3) blood remaining in the body fluid-treating filter device was collected by washing the device using a prescribed amount of a physiological saline solution, and, at the same time, (4) blood was further collected using a prescribed amount of purified water. Then, (5) the amount of blood contained in the liquid collected in (3) and (4) was calculated from the concentration of hemoglobin (hereinafter referred to as "Hb") in the erythrocytes contained in the liquid collected in (3) and (4). The total sum of the blood was regarded as the amount of residual blood.

The flow rate in the operations (1) to (3) above was determined taking the difference in the volume of the body fluid-treating filter devices into consideration. That is, (1) during the blood circulation, 3,000 ml of blood was treated at a flow rate of 50 ml/min in the group with a large capacity (Examples 1 to 3 and Comparative Examples 1, 3, and 4) and 1,500 ml of blood was treated at a flow rate of 25 ml/min in the group with a smaller capacity (Examples 4 to 7 and Comparative Example 2), (2) during the blood collection, 200 ml of a physiological saline solution was caused to flow at a flow rate of 50 ml/min in the group with a large capacity (Examples 1 to 3 and Comparative Examples 1, 3, and 4) and 100 ml of a physiological saline solution was caused to flow at a flow rate of 25 ml/min in the group with a smaller capacity (Examples 4 to 7 and Comparative Example 2), and (3) during washing and collection, 400 ml of a physiological saline solution was caused to flow at a flow rate of 50 ml/min in the group with a large capacity (Examples 1 to 3 and Comparative Examples 1, 3, and 4) and 200 ml of a physiological saline solution was caused to flow at a flow rate of 25 ml/min in the group with a smaller capacity (Examples 4 to 7 and Comparative Example 2). In the above operation (4), 1,000 ml of purified water was caused to flow at a flow rate of 50 ml/min to recover the liquid irrespective of the capacity.

To determine the Hb concentration contained in the recovered liquids, the liquid recovered in the above operation (3) was ten-fold diluted with purified water to hemolyze erythrocytes to measure absorbance at 560 nm, and for the liquid recovered in the above operation (4) the absorbance at 560 nm was measured using the liquid recovered with purified water as is. A calibration curve was prepared using the resulting values of absorbance, based on which the Hb concentration was estimated. For preparing the calibration curve, samples of a two-fold dilution series, up to a 64-fold dilution sample, were prepared using a dilution liquid prepared by ten-fold diluting the blood before treating with purified water to hemolyze erythrocytes. The absorbance at 560 nm was measured for each of the diluted samples using an absorbance meter ("Spectra Thermo" manufactured by TECAN) to prepare the calibration curve. The Hb concentration in cow blood before treating was determined by measuring Hb in a one-day preservation whole blood pool of a cow, to which an anticoagulant was added, using a multi-item automatic blood cell analyzer ("SF-3000" manufactured by Sysmex).

These measured values, the amount of recovered liquids in (3) and (4) were applied to the following formula (I) to calculate the amount of residual blood for each recovered liquid. The total sum was regarded as the residual blood amount of the body fluid-treating filter device.

Residual blood amount (ml)=Recovered washing liquid (ml)×Hb concentration of recovered washing liquid (g/dl)/Hb concentration of blood before treating (g/dl)   (1)

Body fluid recovery performance was evaluated using a body fluid-treating filter device which does not use a flow passage resistant member as a control. That is, the body fluid recovery performance of Examples 1 to 3 and Comparative Examples 3 and 4 was evaluated by the ratio of the residual blood amounts in these Examples and Comparative Examples to the residual blood amount of Comparative Example 1, and the body fluid recovery performance of Examples 4 to 7 was evaluated by the ratio of the residual blood amounts in these Examples to the residual blood amount of Comparative Example 2. When making comparison with Comparative Example 1 or Comparative Example 2, in order to prevent the effects of dispersion according to individual differences of blood, the same blood was treated at the same time in the Examples and Comparative Examples which were compared with Comparative Example 1 or Comparative Example 2.

The results of evaluation are shown in Tables 4-1 and 4-2.

TABLE 4-1

|  | Example | | | Comparative Example | |
|---|---|---|---|---|---|
|  | 1 | 2 | 3 | 3 | 4 |
| Treating pressure increase (100 mmHg>) | YES | YES | YES | YES | NO |
| Amount of residual blood [a] | 51.71 | 45.75 | 40.47 | 64.26 | 56.60 |
| Simultaneously measured amount of residual blood of Comparative Example 1 [b] | 63.55 | 50.42 | 50.42 | 57.87 | 50.78 |
| Body fluid recovery performance [a/b] | 0.81 | 0.91 | 0.80 | 1.11 | 1.11 |

TABLE 4-2

|  | Example | | | |
|---|---|---|---|---|
|  | 4 | 5 | 6 | 7 |
| Treating pressure increase (100 mmHg>) | YES | YES | YES | YES |
| Amount of residual blood [a] | 48.81 | 47.74 | 45.76 | 47.09 |
| Simultaneously measured amount of residual blood of Comparative Example 2 [b'] | 59.61 | 59.61 | 59.61 | 59.61 |
| Body fluid recovery performance [a/b'] | 0.82 | 0.80 | 0.77 | 0.79 |

The results of Examples 1 to 3 and Comparative Examples 1, 3, and 4 indicate that treating pressure easily increases in the case in which the inner side spacer layer is not provided. The results of Examples 1 to 7 and Comparative Examples 1 and 2 indicate that no significant increase of the treating pressure that might induce a clinical problem occurs and the body fluid recovery performance increases irrespective of the differences in the length and cross-sectional shape of the housing, if the thickness of the spacer layer is within a certain range. The results of Examples 1 and 3 and Comparative Example 4 indicate that there is a lower limit to the thickness of the spacer, and the results of Examples 1 and 2 and Comparative Example 3 indicate that there is an upper limit to the thickness of the spacer.

In Examples 4 to 7 and Comparative Example 3, the ratio of the volume of the flow passage resistant member to the hollow section increases in the order of Example 4, Comparative Example 3, Example 5, Example 6, and Example 7. The amount of residual blood, however, was large in Comparative Example 3, indicating that not only the volume and length of the flow passage resistant member are important, but also the thickness of the spacer layer must be within a specific range.

Although the above Examples and Comparative Examples were described referring to a structure in which the body fluid flow port connected to the outer circumference of the body fluid-treating filter layer is used as the inlet port and the body fluid flow port connected to the inner circumference of the body fluid-treating filter layer is used as the outlet port, the flow passage resistance remains the same when the inlet port and the outlet port are reversed (when the body fluid flows in the reverse direction). Accordingly, the same results are obtained irrespective of the flow direction.

Although the effect of the thickness of a spacer layer was evaluated in the inner side spacer layer between the flow passage resistant member and inner circumference of the body fluid-treating filter layer, the same results will be obtained when evaluating in the outer side spacer layer between the outer circumference of the flow passage resistant member layer and the inner circumference of the housing. Since the thickness of the outer side spacer layer is in a rage of 0.7 mm to 3.5 mm at all points, there is almost no probability that the decrease in the pressure loss in the outer side spacer layer will affect the flow of blood.

Although several embodiments of the present invention have been described in detail, the present invention is not limited to the above-mentioned embodiments, various changes and modifications of the design being possible within the scope of the claims.

For example, the specification may be changed to the extent that cells and the like contained in a body fluid are not damaged. The treating pressure is generally required not to exceed 100 mmHg due to problems such as hemolysis. It is important to appropriately select the flow amount, the shape of the device, and the filter material, because the treating pressure varies according to these conditions and materials. More specifically, when the treating pressure increases due to the increase in the amount of body fluid to be treated, the increase in the treating pressure can be controlled by controlling an increase in the treating linear velocity in the filter layer by increasing the length of the device, while maintaining the same cross-sectional shape as in the embodiment of the present invention. Alternatively, the increase in the treating pressure can be controlled by enlarging the filtration cross-sectional area, while using the device with the same length.

It is also possible to adjust the entrapping performance or adsorption performance of the filter material by replacing the filter material with another material having a smaller resistance without changing the cross-sectional shape or the length of the device, provided that in order to sufficiently fill the inside of the filter device with a body fluid during body fluid-treating, it is necessary that the body fluid throughput is larger than the volume of the space in the device including the volume of the voids in the filter material.

The amount of the body fluid treated by the body fluid-treating filter device of the present invention is typically from 300 to 3,000 ml, the flow rate is typically from 10 to 200 ml/min, and the priming volume of the body fluid-treating filter device is typically from 10 to 500 ml.

INDUSTRIAL APPLICABILITY

The body fluid-treating filter device of the present invention is useful for removing specific proteins, leukocytes, toxins, and the like contained in body fluids of patients to be applied to an extracorporeal circulation blood purification therapy of curing autoimmune diseases, such as systemic lupus erythematosus, chronic or malignant articular rheumatism, multiple sclerosis, chronic ulcerative colitis, and Crohn's disease, as well as other diseases such as sepsis, inflammatory bowel disease, leukemia, and cancer, or for immunity control before an organ transplant operation.

The invention claimed is:

1. A cylindrical body fluid-treating filter device comprising a cylindrical housing which has two body fluid flow ports and a body fluid-treating cylindrical filter layer housed in the cylindrical housing, the cylindrical filter layer being disposed so as to divide the inner space of the housing into two hollow sections by liquid-tightly sealing the both ends and securing at least one end thereof to the inner wall of the housing, one of the hollow sections of the housing divided by the cylindrical filter layer communicating with the first body fluid flow port, and the other hollow section in the housing divided by the cylindrical filter layer communicating with the second body fluid flow port, wherein a rod-shaped flow passage resistant member extends through the hollow section along the center axis formed by the cylindrical filter layer, and a spacer layer for allowing a body fluid to flow with a thickness of not less than 0.7 mm, but not more than 3.5 mm, is provided between the outer circumference of the cylindrical filter layer and the housing, and between the inner peripheral surface of the cylindrical filter layer and the flow passage resistant member.

2. The cylindrical body fluid-treating filter device according to claim 1, wherein the spacer layer for flowing a body fluid with a thickness of not less than 0.7 mm, but not more than 3.5 mm, provided between the inner peripheral surface of the cylindrical filter layer and the flow passage resistant member extends ¼ to 15/16 of the length of the hollow section from one end of the cylindrical filter layer.

3. The cylindrical body fluid-treating filter device according to claim 1, wherein the flow passage resistant member has a shape of which the cross-sectional area is fixed on the side near the end of the cylindrical filter layer, but continuously or intermittently decreases toward the other end.

4. The cylindrical body fluid-treating filter device according to claim 2, wherein the flow passage resistant member has a shape of which the cross-sectional area is fixed on the side near the end of the cylindrical filter layer, but continuously or intermittently decreases toward the other end.

* * * * *